US010321984B2

(12) United States Patent
Lonn et al.

(10) Patent No.: US 10,321,984 B2
(45) Date of Patent: Jun. 18, 2019

(54) SPIRAL FLOW INDUCING STENT AND CANULA CUT METHOD OF MAKING SAME (71) Applicant: Cook Medical Technologies LLC, Bloomington, IN (US)

(72) Inventors: Melissa Lonn, Lafayette, IN (US); Adam Shields, Lafayette, IN (US); Keith Milner, West Lafayette, IN (US); Seoggwan Kim, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/381,408

(22) Filed: Dec. 16, 2016

(65) Prior Publication Data

US 2017/0239034 A1    Aug. 24, 2017

Related U.S. Application Data (60) Provisional application No. 62/297,311, filed on Feb. 19, 2016.

(51) Int. Cl.
| | |
|---|---|
| *A61F 2/06* | (2013.01) |
| *A61F 2/88* | (2006.01) |
| *A61F 2/848* | (2013.01) |
| *A61F 2/91* | (2013.01) |
| *A61F 2/82* | (2013.01) |

(52) U.S. Cl.
CPC ............... *A61F 2/06* (2013.01); *A61F 2/848* (2013.01); *A61F 2/88* (2013.01); *A61F 2/91* (2013.01); *A61F 2002/068* (2013.01); *A61F 2002/825* (2013.01); *A61F 2002/8483* (2013.01); *A61F 2210/0014* (2013.01); *A61F 2220/0091* (2013.01); *A61F 2230/0091* (2013.01); *A61F 2240/001* (2013.01)

(58) Field of Classification Search
CPC ............................ A61F 2/82; A61F 2/88–2/85
USPC ................................. 623/1.15–1.22
See application file for complete search history.

(56) References Cited

U.S. PATENT DOCUMENTS

| 7,682,673 | B2 | 3/2010 | Houston et al. | |
|---|---|---|---|---|
| 2002/0116044 | A1* | 8/2002 | Cottone, Jr. ............. | A61F 2/88 623/1.2 |
| 2003/0195609 | A1* | 10/2003 | Berenstein ............. | A61F 2/856 623/1.15 |
| 2004/0176832 | A1* | 9/2004 | Hartley .................... | A61F 2/07 623/1.11 |

(Continued)

OTHER PUBLICATIONS

European Patent Office, European Search Report for Application No. 17156732.4, Published Jun. 9, 2017, Munich Germany.

*Primary Examiner* — Suzette J Gherbi
(74) *Attorney, Agent, or Firm* — Liell & McNeil (57) ABSTRACT A cannula cut spiral flow inducing stent includes a plurality of spiral inducing flow diverters that each include a piece of sheet metal with a helically shaped flow surface. A proximal stent region, which includes a plurality of first struts, is joined to a proximal end of each of the spiral inducing flow diverters. A distal stent region, which includes a plurality of second struts, is joined to a distal end of each of the spiral inducing flow diverters. All of the first struts and all of the second struts share a cannula thickness, but the shaped pieces of sheet metal may have a lesser thickness.

20 Claims, 5 Drawing Sheets

(56) References Cited

U.S. PATENT DOCUMENTS

| | | | |
|---|---|---|---|
| 2004/0186556 A1* | 9/2004 | Hogendijk | A61F 2/88 623/1.16 |
| 2004/0186561 A1* | 9/2004 | McGuckin, Jr. | A61B 17/12109 623/1.36 |
| 2005/0033410 A1* | 2/2005 | Hogendijk | A61F 2/07 623/1.15 |
| 2005/0159803 A1* | 7/2005 | Lad | A61F 2/07 623/1.13 |
| 2007/0005126 A1* | 1/2007 | Tischler | A61F 2/91 623/1.15 |
| 2007/0129786 A1* | 6/2007 | Beach | A61F 2/91 623/1.15 |
| 2007/0270939 A1 | 11/2007 | Hood et al. | |
| 2008/0140176 A1 | 6/2008 | Krause et al. | |
| 2008/0221663 A1* | 9/2008 | Leopold | A61F 2/885 623/1.18 |
| 2008/0294240 A1* | 11/2008 | Casey | A61F 2/915 623/1.16 |
| 2012/0123327 A1* | 5/2012 | Miller | A61M 25/0012 604/95.04 |
| 2012/0296408 A1* | 11/2012 | Jones | A61B 17/12 623/1.11 |
| 2013/0110221 A1* | 5/2013 | Campbell | A61F 2/04 623/1.2 |
| 2014/0343664 A1* | 11/2014 | Furey | A61F 2/06 623/1.18 |
| 2015/0045784 A1 | 2/2015 | Kunis | |
| 2015/0051694 A1* | 2/2015 | Furey | A61F 2/82 623/1.15 |
| 2016/0143757 A1* | 5/2016 | Nissl | A61F 2/915 623/1.16 |
| 2016/0213500 A1* | 7/2016 | Beger | A61B 17/025 |
| 2017/0231640 A1* | 8/2017 | Furey | A61B 17/12031 606/200 |

* cited by examiner

SPIRAL FLOW INDUCING STENT AND CANULA CUT METHOD OF MAKING SAME

TECHNICAL FIELD

The present disclosure relates generally to devices for inducing spiral blood flow in a blood vessel, and more particularly to a spiral flow inducing stent that includes spiral inducing flow diverters flanked by proximal and distal stent regions.

BACKGROUND

Due in part to the lack of transplant availability, many patients with end-stage renal disease receive regular hemodialysis treatments. To minimize treatment time, hemodialysis requires a large blood volume flow rate that is typically achieved through the surgical creation of an arteriovenous shunt. This creates a low resistance pathway that results in significantly increased flow rates through a graft or an arteriovenous fistula (AVF). After surgical creation of an AVF, the inflow and outflow vessels must dilate sufficiently, and the venous tissue must undergo a remodeling process known as "fistula maturation" in order to be able to sustain the high flow rates necessary for hemodialysis. One common problem with AVFs is tissue proliferation along the lumen of the vein known as neointimal hyperplasia (NIH), which can lead to stenosis, reduced flow, and ultimately failure of the fistula. The progression of NIH may be, in part, the venous tissue's response to the abnormal hemodynamic stresses which result from the increased flow rates and large pressure drop across an arteriovenous anastomosis. The abnormal flow through an AVF appears to be generally turbulent rather than laminar.

Several reports suggest that the native state of arterial blood flow may exhibit circumferentially oriented velocity components such that the blood flow is helical or spiral in nature. The spiral blood flow is thought to play a roll in maintaining healthy vascular function. Thus, it may be possible that creating spiral blood flow in the vicinity of an AVF could help prevent or slow the progression of NIH.

The present disclosure is directed toward one or more of the problems set forth above.

SUMMARY OF THE DISCLOSURE

In one aspect, a spiral flow inducing stent includes a plurality of spiral inducing flow diverters that each include a piece of sheet metal with a helically shaped flow surface. A proximal stent region, which includes a plurality of first struts, is joined to a proximal end of each of the spiral inducing flow diverters. A distal stent region, which includes a plurality of second struts, is joined to a distal end of each of the spiral inducing flow diverters. All of the first struts and all of the second struts share a cannula thickness.

In another aspect, a method of making a spiral flow inducing stent includes cutting away a pattern of material from a cannula to leave a plurality of sheets of metal. The sheets of metal are bent to define a helically shaped flow surface. The helical shape corresponding to the helically shaped flow surface in each of the sheets of metal is set. A pattern of material is cut away from a segment of the cannula proximal to the sheets of metal into a proximal stent region with a plurality of first struts. A pattern of material is cut away from a segment of the cannula distal to the sheets of metal into a distal stent region with a plurality of second struts.

DETAILED DESCRIPTION

Figure 1:
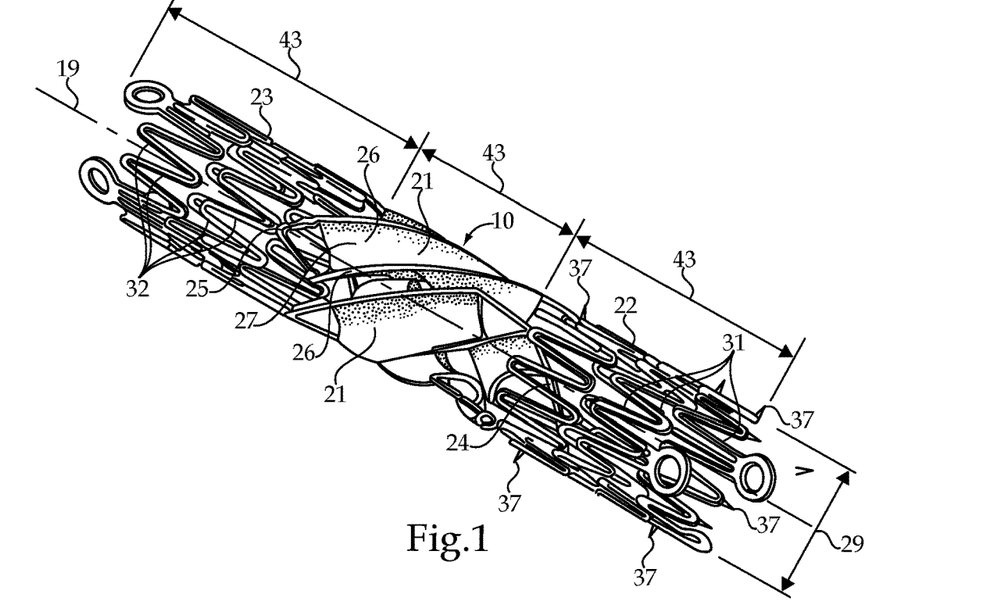
FIG. 1 is a perspective view of a spiral flow inducing stent according to the present disclosure.
Figure 2:
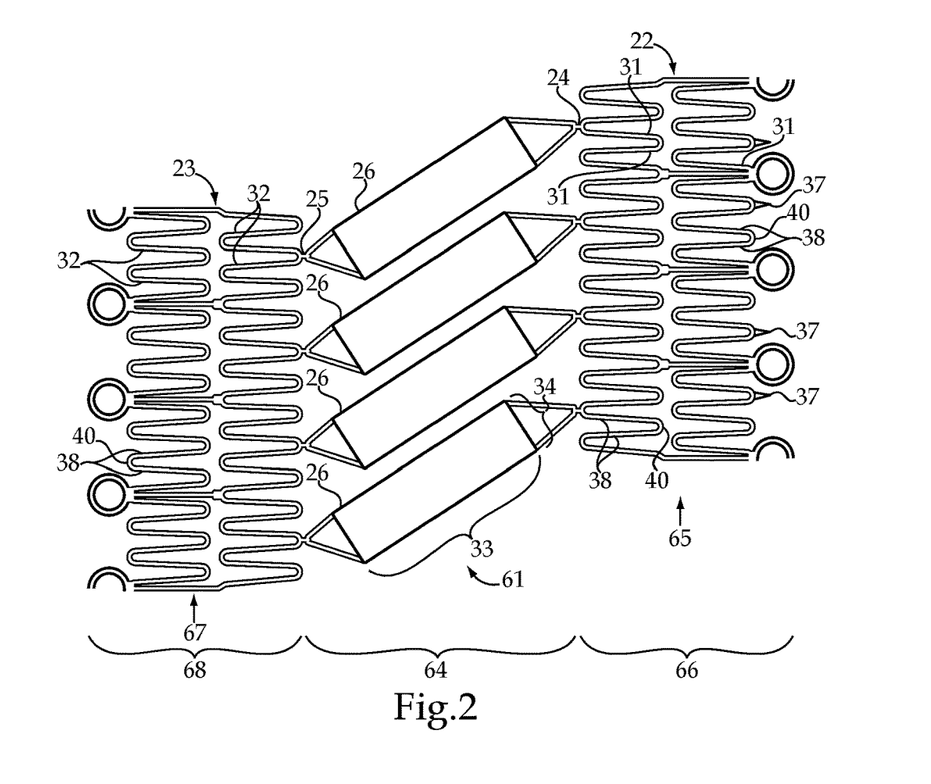
FIG. 2 is a flattened pattern to be cut from a cannula to produce the spiral flow inducing stent of FIG. 1.
Figure 13:
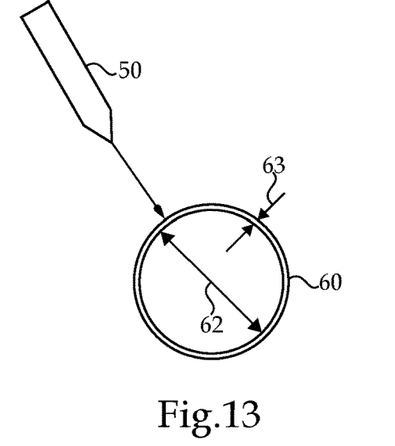
FIG. 13 is an end view of a cannula being laser cut into a stent according to according to an aspect of the present disclosure.

Referring initially to FIGS. 1 and 2, a spiral flow inducing stent 10 includes a plurality of spiral inducing flow diverters 21 that each include a piece of sheet metal 26 with a helically shaped flow surface 27. A proximal stent region 22, which includes a plurality of first struts 31, is joined to a proximal end 24 of each of the spiral inducing flow diverters. A distal stent region 23, which includes a plurality of second struts 32, is joined to a distal end 25 of each of the spiral inducing flow diverters 21. As the spiral flow inducing stent 10 is cut from a cannula, all of the first struts 31 and all of the second struts 32 share a cannula thickness 63 (FIG. 13). In the illustrated embodiment, the spiral flow inducing stent 10 includes exactly 4 spiral inducing flow diverters 21. However, any number of spiral inducing flow diverters from two or more would also fall within the intended scope of the present disclosure. The spiral flow inducing stent 10 may be cut from a cannula of any suitable metallic alloy. However, in the event that the spiral flow inducing stent 10 is made to be self expanding, the stent 10 may be cut from a cannula of a suitable shape memory metallic alloy, such as nitinol. Alternatively, spiral flow inducing stent 10 could also be balloon expanded without departing from the present disclosure. Although not necessary, spiral flow inducing stent 10 may include a number of eyelets on opposite ends for receiving radiopaque gold rivets for better in vitro visualization in a manner well known in the art. In addition, spiral flow inducing stent 10 may also include a plurality of tissue engaging barbs 37 extending radially outward from at least one of the proximal stent region 22 and the distal stent region 23. These tissue engaging barbs 37 may assist in preventing the spiral flow inducing stent 10 from migrating after being implanted in a vessel. If included at all, the tissue engaging barbs 37 may only appear in one of the proximal stent region 22 and distal stent region 23 because the spiral flow inducing stent 10 may tend to change slightly in length as its diameter changes, such as due to maturation of an arteriovenous fistula, AVF.

Because spiral flow inducing stent 10 is preferably cannula cut, all portions of the proximal stent region 22, the distal stent region 23 and the spiral inducing flow diverters 21 may be integral with each other. As used in the present disclosure, integral means that the various parts have a same origin and thus have never been disconnected from one another or required connection through some other means, such as a weld. Thus, two parts that are welded to one another to form a whole cannot be considered to be integral in the context of the present disclosure. Although not necessary, the proximal stent region 22, the distal stent region 23 and the spiral inducing flow diverters 21 may have longitudinal lengths 43 along a longitudinal axis 19 that are about equal. In the context of the present disclosure the term "about equal" means that the ratio of any two longitudinal lengths 43 when rounded to a single significant digit will be the numeral one. Nevertheless, a spiral flow inducing stent 10 having substantially different longitudinal lengths 43 could also fall within the scope of the present disclosure. In the illustrated embodiment, the proximal stent region 22 is identical to the distal stent region 23. Nevertheless, spiral flow inducing stent having a proximal stent region that is dissimilar to the distal stent region would also fall within the intended scope of the present disclosure.

Referring in addition to FIGS. 13-18, the spiral flow inducing stent 10 of FIG. 1 may be cut from a cannula 60 in the pattern shown in FIG. 2, such as by utilizing a laser cutter 50 in a manner well known in the art. In general, cannula 60 will have a uniform cannula diameter 62 and a uniform cannula thickness 63. Initially, the pattern 61 of material may be cut away from cannula 60 to leave a plurality of sheets of metal 26 as shown in FIG. 2. Each of the pieces of sheet metal 26 may have a length 33 that is greater than a width 34. In some embodiments, in order to increase the area of the helically shaped flow surface 27, the individual pieces of sheet metal 26 may be stretch along the width dimension, with the end result being that the spiral inducing flow diverters 21 end up of having a thickness 35 that is less than the cannula thickness 63. Preferably, this stretching along the width dimension is accompanied by forming the individual pieces of sheet metal 26 to define an open channel 36 that extends along the length 33. Preferably, the open channels 36 open radially outward relative to the longitudinal axis 19.

Figure 3:
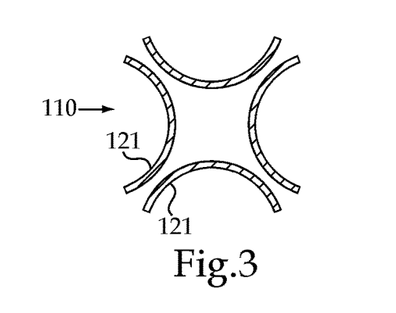
FIG. 3 is a sectioned view through spiral inducing flow diverters for the spiral flow inducing stent of FIG. 1.
Figure 4:
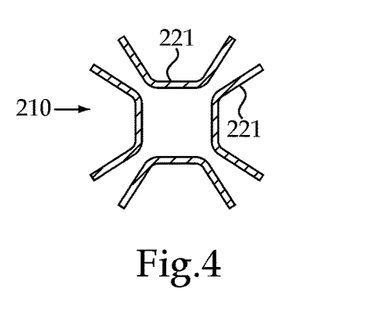
FIG. 4 is a cross section of spiral flow diverters according to another aspect of the present disclosure.
Figure 5:
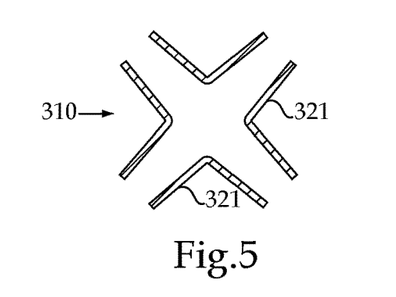
FIG. 5 is a sectioned view through spiral inducing flow diverters according to another aspect of the present disclosure.
Figure 6:
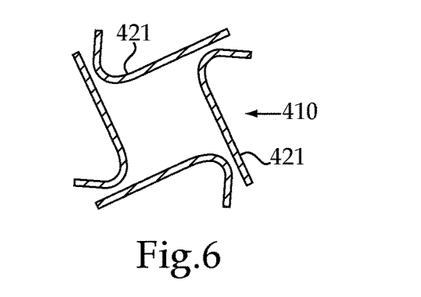
FIG. 6 is a sectioned view through spiral inducing flow diverters according to still another aspect of the present disclosure.
Figure 14:
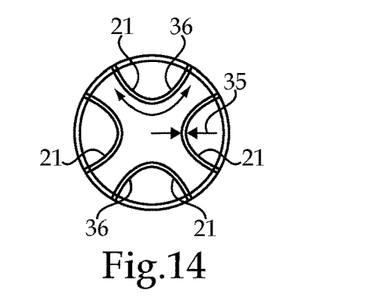
FIG. 14 shows the partially constructed stent after being cut and having portions of the cannula wall bent into flow diverters.
Figure 15:
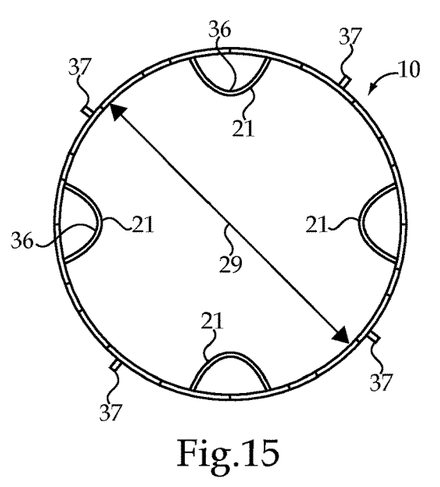
FIG. 15 shows an end view of the stent of FIG. 14 after being expanded in diameter for heat setting.

In the embodiment of FIG. 1, the spiral inducing flow diverters 21 may have a cross section that resembles an arch, as best shown in FIGS. 14 and 15. Nevertheless, a wide variety of different shaped channels could also fall within the intended scope of the present disclosure. For instance, FIG. 3 shows a section through a spiral flow inducing stent 110 in which the spiral inducing flow diverters 21 have a cross section that resembles the arc of a circle. FIG. 4 shows a section through a spiral flow inducing stent 210 in which the spiral inducing flow diverters 221 have three sided shape that resembles a portion of a trapezoid. FIG. 5 shows a section through a spiral flow inducing stent 310 in which the spiral inducing flow diverters 321 have a V shaped cross section. Finally, FIG. 6 shows a section through a spiral flow inducing stent 410 in which a sectioned view of the spiral inducing flow diverters 21 have a asymmetrical J shape. Nevertheless, all of the embodiments of FIGS. 1-6 all include open channels 36 that open radially outward relative to a longitudinal axis 19 of the underlying spiral flow inducing stent 10, 110, 210, 310, 410.

Figure 7:
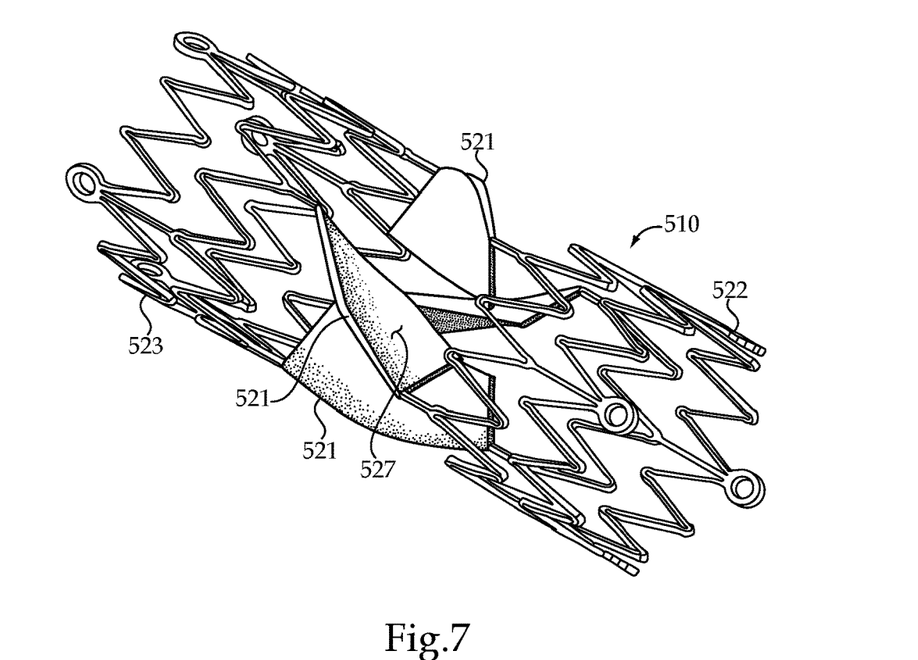
FIG. 7 is a perspective view of a spiral flow inducing stent according to another embodiment of the present disclosure.
Figure 8:
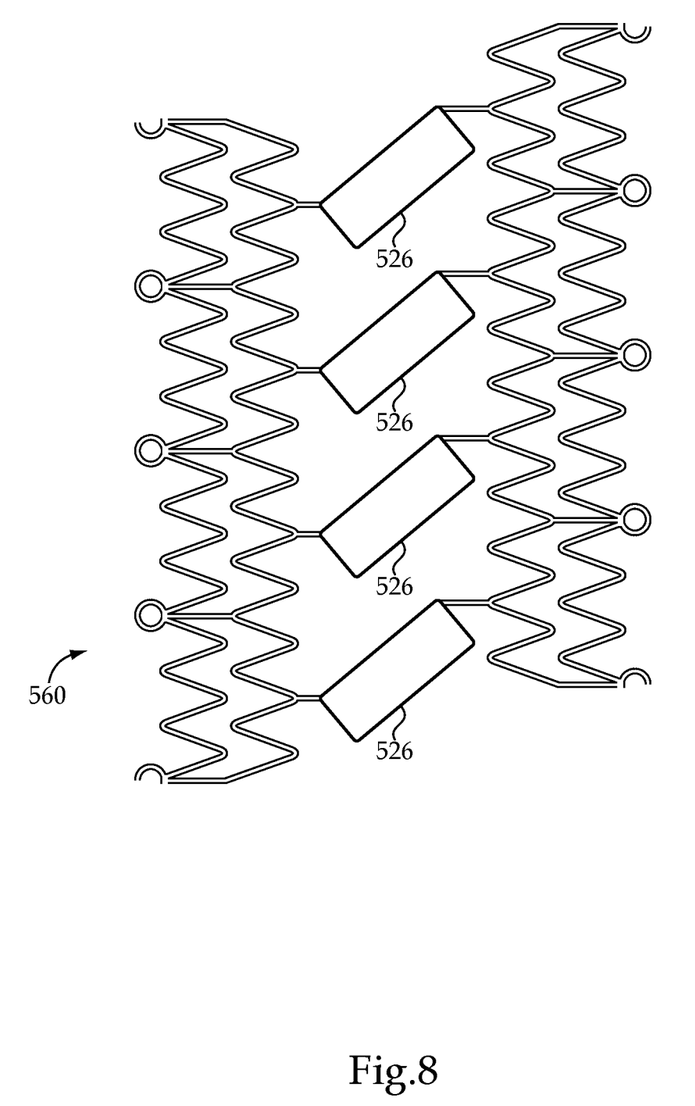
FIG. 8 is a flattened pattern to be cut from a cannula to produce the spiral flow inducing stent of FIG. 7.
Figure 9:
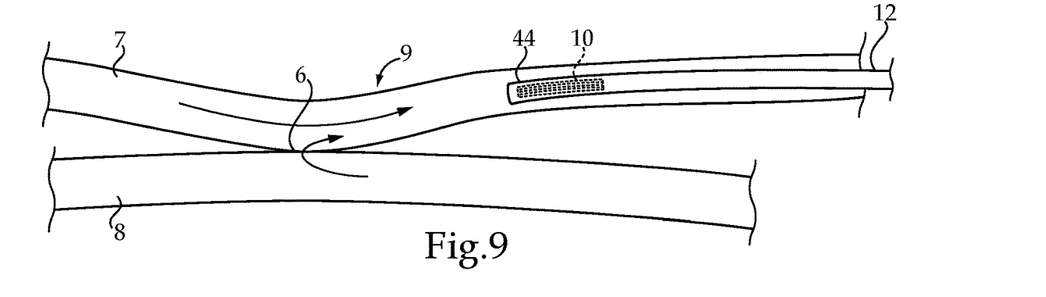
FIG. 9 is a side view of an AVF during delivery of a spiral flow inducing stent according to the present disclosure.
Figure 10:
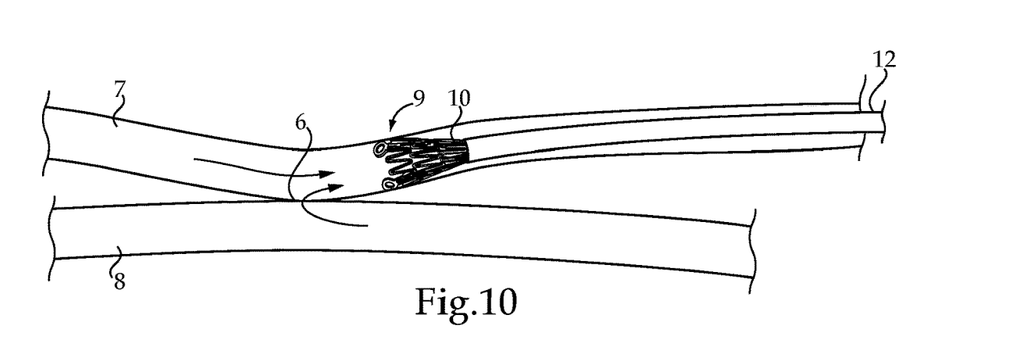
FIG. 10 is a view similar to FIG. 9 during deployment of a spiral flow inducing stent according to the present disclosure.
Figure 11:
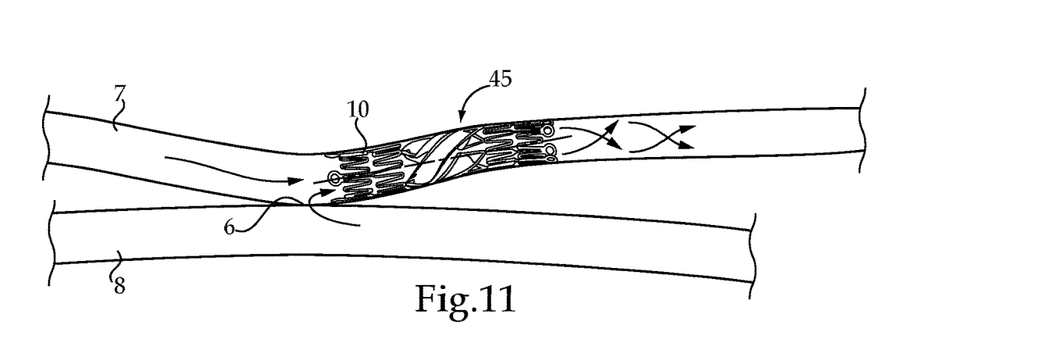
FIG. 11 is a side view of the AVF of FIGS. 9 and 10 after the spiral flow inducing stent has been implanted.
Figure 12:
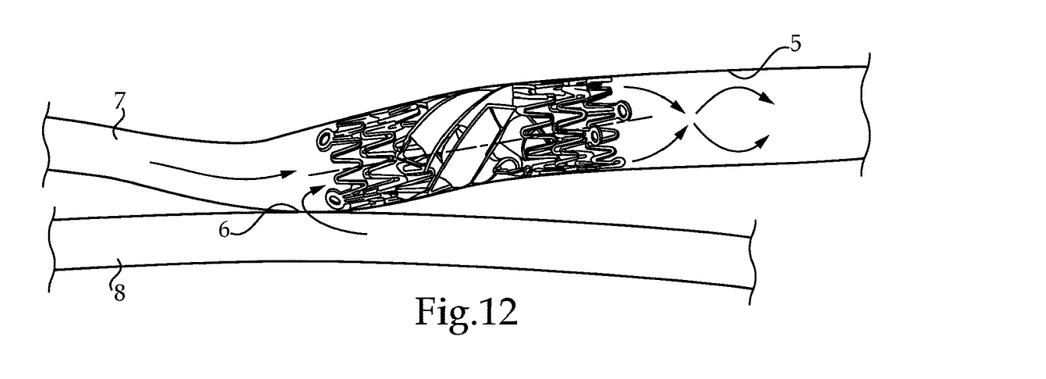
FIG. 12 is a side view of the AVF of FIGS. 9-11 after the vein diameter has enlarged over time.

Referring now in addition to FIGS. 7 and 8, a spiral flow inducing stent 510 is similar to the earlier described embodiments in that it includes a plurality of spiral inducing flow diverters 521 that each include a helically shaped flow surface 527 that is attached at one end to a proximal stent region 522 and attached at an opposite end to a distal stent region 523. However, spiral flow inducing stent 510 differs from the earlier described stents in that each of the spiral inducing flow diverters 521 is formed to include a helically shaped flow surface 27 but without the open channel configuration of the earlier embodiments. The spiral flow inducing stent 510 may be cut from a cannula using pattern 560 shown in FIG. 8 to include a plurality of sheets of metal 526 that are individually twisted and set to define a helically shaped flow surface 527.

In all of the illustrated embodiments, because the struts 31 and 32 are all cut from the same cannula 60, each of the stent regions 22 and 23 include a plurality of different pairs 38 of first struts 31 and second struts 32 that are attached to a respective living hinge 40. Those skilled in the art will appreciate that this construction is well known in the art. In the event that the stent 10 is to be self expanding, each living hinge vertex 40 may be biased toward a spread configuration so that each of the proximal stent region 22 and distal stent region 23 are self expanding. In the illustrated embodiment, each of the spiral inducing flow diverters 21 has its proximal end attached to a respective living hinge vertex 40 of the proximal stent region 22, and has the distal end 25 attached to a respective living hinge vertex 40 of the distal stent region 23. In the event that a spiral flow inducing stent 10 has each of its segments cut from a common cannula, the attachment of the proximal stent region 22 and distal stent region 23 to the spiral inducing flow diverters 21 is a result of the various features being integral with one another, rather than being attached through some connective strategy, such as a weld. Nevertheless, a spiral flow inducing stent in which the proximal stent region 22 spiral inducing flow diverters 21 and distal stent region 23 are cut from different cannulas and then later joined, such as via a weld, would also fall within the intended scope of the present disclosure.

Figure 16:
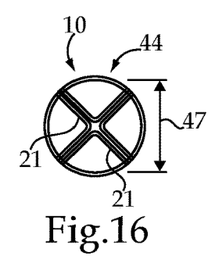
FIG. 16 is an end view of the stent of FIGS. 14 and 15 after being compressed to a transport diameter.
Figure 17:
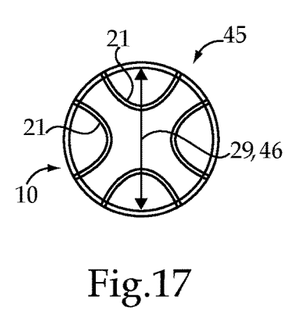
FIG. 17 is an end view of the stent of FIG. 16 expanded to an implanted diameter.
Figure 18:
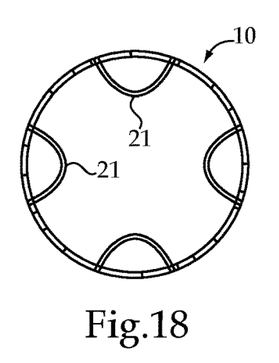
FIG. 18 shows the stent of FIG. 17 diameter growth after implantation.

Referring again to FIGS. 2 and 13-15, and in addition to FIGS. 16-18, a method of making the spiral flow inducing stent 10 of FIG. 1 includes cutting away a pattern 61 of material from cannula 60 to leave a plurality of sheets of metal 26. This aspect is shown in FIGS. 2 and 13 respectively. Next, the sheets of metal 26 are bent to define a helically shaped flow surface 27. In the case of the embodiment of FIGS. 7 and 8, the spiral inducing flow diverters 21 retain a common cannula thickness 63 with the struts that comprise the proximal stent region 522 and the distal stent region 523. However, in the event that the pieces of sheet metal 26 are bent to include the open channels 36 as shown in the embodiments of FIGS. 1-6, the bending step may include plastically deforming each of the pieces of metal 26 into an open channel 36 extending along length 33. For instance, this may be accomplished by stretching the pieces of sheath metal 26 along the width 34 forming the individual open channels 36 and then bending the same into a helically shaped flow surface 27. Thereafter, the shape of the spiral inducing flow diverters 21 may be set using a manner known in the art, such as heat setting in the event that the original cannula was formed of nitinol. Next, the pattern 65 of material may be cut away from a segment 66 of cannula 60 proximal to the sheets of metal 26 to create the proximal stent region 22 that includes a plurality of first struts 31. Next, a pattern 67 of material may be cut away from a segment 68 of cannula 60 distal to the sheets of metal 26 to create the distal stent region 23 with a plurality of second struts 32. After this cutting procedure, the partially completed stent 10 may be radially expanded to a diameter that is two or more times the diameter of the original cannula 60 and then have that diameter set, such as heat setting in a manner known in the art. In addition, the tissue engaging barbs 37, if included, may also be bent to point radially outward as shown in FIG. 15. The expanded diameter of FIG. 15 may be accomplished by expanding the proximal stent region 22 and the distal stent region 23 to a stent diameter 29 that is about twice a diameter of cannula 60. Thereafter, the spiral flow inducing stent 10 may be electropolished, such as to smooth out the various exposed wetted surfaces and debur the finished stent.

In one specific application, the cannula diameter 62 may be 3 millimeters, the transport diameter 47 in the transport configuration 44 may be 2 millimeters, and the implanted diameter 46 may at the time of initial implantation (FIG. 17) have a stent diameter 21 that is about equal to the cannula diameter 62. As used in the present disclosure, about twice means that when rounded to a single significant digit, the ratio of the one thing to the other will be two. Likewise, as used in the present disclosure, the phrase "about equal" means that the ratio of the two dimensions in question, when rounded to a single significant digit, will be one. In the event that the spiral flow inducing stent is utilized in an AVF, FIG. 18 shows that the stent 10 can grow in diameter as the vessel dilates during fistula maturation of the AVF in a manner known in the art. However, the spiral inducing flow diverters 21 may remain substantially unchanged or change when the diameter of the stent increases, as best shown in FIGS. 17 and 18. Thus, in one specific example, the cannula diameter 62 may be three millimeters, the transport diameter 47 of the stent 10 in the transport configuration 44 may be 2 millimeters, and the stent diameter 29 at the initially implanted diameter 46 may be 3 millimeters. The stent diameter 29 during the manufacturing step shown in FIG. 15 where the proximal and distal stent regions are heat set to a large diameter of maybe 7 millimeters. In the case of a self expanding stent, the spiral flow inducing stent 10 will be elastically compressed in the transport configuration 44.

INDUSTRIAL APPLICABILITY

The present disclosure finds general applicability to devices for inducing spiral blood flow in a vessel. The present disclosure finds specific applicability to implantation in the vicinity of an arteriovenous fistula (AVF) in order to undermine or inhibit neointimal hyperplasia.

Referring now in addition to FIGS. 9-12, a method of impeding neointimal hyperplasia with a spiral blood flow device 10 includes moving the spiral blood flow device 10 in a transport configuration 44 to an implantation site 9. For instance, a spiral blood flow device 10 may be compressed and carried to implantation site 9 using a suitable delivery device 12 in a manner well known in the art with regard to the delivery of self expanding stents. After arrival at implantation site 9, the spiral blood flow device 10 is implanted at the implantation site 9 at least in part by expanding the stent to a first diameter (FIG. 14) in a continuum of expanded configurations. During the implantation, one could expect the spiral inducing flow diverters 21 to resiliently unfold or unfurl from a compressed state to the shape and orientation shown. After implantation, the spiral inducing flow diverters 21 induce spiral flow in blood flowing through device 10, as best shown by the arrows in FIGS. 11 and 12. Although not necessary, spiral blood flow device 10 is shown being implanted in the vicinity of an AVF 6 that fluidly joins an artery 8 to a vein 7 in a manner well known in the art. As the AVF matures, the vessel 5 may tend to increase in diameter, such as grow from a first diameter, as shown in FIG. 17 to a second diameter as shown in FIG. 18. When this occurs, the helical flow angle defined the spiral inducing flow diverters 21 may decrease, increase or remain constant throughout the change from the first diameter to the second diameter.

In the case of a self expanding stent 10, the implantation may be accomplished using known techniques by releasing the spiral blood flow device 10 to self expand at the implantation site 9. However, in the event that the stent 10 is a balloon expanded stent, the implantation might include inflating a balloon to facilitate implantation at the implantation site 9 in a manner well known in the art. During implantation, one could expect the plurality of first struts 31 and the plurality of second struts 32 to move into contact with the wall of vessel 5. In the event that the spiral flow inducing device 10 is delivered to an implantation site 9 in proximity to an AVF 6, one could expect the diameter of the self expanding stent 10 to range from between two millimeters to six millimeters over the continuum of expanded configurations. Nevertheless, one could expect in a typical application for the diameter of the vessel 5 to dilate up to roughly 150% of the original diameter (FIG. 11) up to the enlarged diameter FIG. 12. Although FIGS. 9-12 show a side-to-side AVF, the stent 10 could also be used in an end-to-side AVF. For instance, the proximal end of the stent 10 could be positioned in the artery/anastomosis, with the rest of the stent in the vein.

The present description is for illustrative purposes only, and should not be construed to narrow the breadth of the present disclosure in any way. Thus, those skilled in the art will appreciate that various modification might be made to the presently disclosed embodiments without departing from the full and fair scope and spirit of the present disclosure. Other aspects, features and advantages will be apparent upon an examination of the attached drawings and appended claims.

What is claimed is:

1. A spiral flow inducing stent comprising:
   a plurality of spiral inducing flow diverters that each include a piece of sheet metal with a helically shaped flow surface;
   a proximal stent region, which includes a plurality of first struts, joined to a proximal end of each of the spiral inducing flow diverters;
   a distal stent region, which includes a plurality of second struts, joined to a distal end of each of the spiral inducing flow diverters;
   all of the first struts and all of the second struts share a cannula thickness; and the helically shaped flow surface is closer to a stent centerline than the first struts and the second struts.

2. A spiral flow inducing stent comprising:
a plurality of spiral inducing flow diverters that each include a piece of sheet metal with a helically shaped flow surface;
a proximal stent region, which includes a plurality of first struts, joined to a proximal end of each of the spiral inducing flow diverters;
a distal stent region, which includes a plurality of second struts, joined to distal end of each of the spiral inducing flow diverters;
all of the first struts and all of the second struts share a cannula thickness; and
wherein each of the pieces of sheet metal has a length that is greater than a width, and has a thickness that is less than the cannula thickness.

3. The spiral flow inducing stent of claim 2 wherein each of pieces of sheet metal defines an open channel extending along the length.

4. The spiral flow inducing stent of claim 3 wherein each of the open channels opens radially outward relative to a longitudinal axis.

5. A spiral flow inducing stent comprising:
a plurality of spiral inducing flow diverters that each include a piece of sheet metal with a helically shaped flow surface;
a proximal stent region, which includes a plurality of first struts, joined to a proximal end of each of the spiral inducing flow diverters;
a distant stent region, which includes a plurality of second struts, joined to a distal end of each of the spiral inducing flow diverters;
all of the first struts and all of the second struts share a cannula thickness; and
wherein each of a plurality of different pairs of the first struts are attached to a respective living hinge vertex.

6. The spiral flow inducing stent of claim 5 wherein each living hinge vertex is biased toward a spread configuration so that each of the proximal stent region and the distal stent region are self expanding.

7. A spiral flow inducing stent comprising:
a plurality of spiral inducing flow diverters that each include a piece of sheet metal with a helically shaped flow surface;
a proximal stent region, which includes a plurality of first struts, joined to a proximal end of each of the spiral inducing flow diverters;
a distal stent region, which includes a plurality of second struts, joined to a distal end of each of the spiral inducing flow diverters;
all of the first struts and all of the second struts share a cannula thickness; and
including exactly four spiral inducing flow diverters.

8. The spiral flow inducing stent of claim 1 wherein the proximal stent region is identical to the distal stent region.

9. The spiral flow inducing stent of claim 1 wherein the proximal stent region, the distal stent region and the spiral inducing flow diverters have longitudinal lengths along a longitudinal axis that are about equal.

10. The spiral flow inducing stent of claim 1 which is movable between a transport configuration and an implanted configuration;
wherein the spiral flow inducing stent has a transport diameter in the transport configuration that is less than a cannula diameter, and has a implanted diameter in the implanted configuration that is about equal to the cannula diameter.

11. The spiral flow inducing stent of claim 1 including a plurality of tissue engaging barbs extending radially outward from at least one of the proximal stent region and the distal stent region.

12. The spiral flow inducing stent of claim 1 wherein all portions of the proximal stent region, the spiral inducing flow diverters and the distal stent region are integral with each other.

13. A spiral flow inducing stent comprising:
a plurality of spiral inducing flow diverters that each include a piece of sheet metal with a helically shaped flow surface;
a proximal stent region, which includes a plurality of first struts, joined to a proximal end of each of the spiral inducing flow diverters;
a distal stent region, which includes a plurality of second struts, joined to a distal end of each of the spiral inducing flow diverters;
all of the first struts and all of the second struts share a cannula thickness; and
wherein each of the spiral inducing flow diverters has the proximal end attached to a respective living hinge vertex of the proximal stent region, and has the distal end attached to a respective living hinge vertex of the distal stent region.

14. A method of making a spiral flow inducing stent that includes a plurality of spiral inducing flow diverters that each include a piece of sheet metal with a helically shaped flow surface; a proximal stent region, which includes a plurality of first struts, joined to a proximal end of each of the spiral inducing flow diverters; a distal stent region, which includes a plurality of second struts, joined to a distal end of each of the spiral inducing flow diverters; all of the first struts and all of the second struts share a cannula thickness, the helically shaped flow surface is closer to a stent centerline than the first struts and the second struts the method comprising the steps of:
cutting away a pattern of material from a cannula to leave the plurality of sheets of metal;
bending the sheets of metal to define the helically shaped flow surface;
setting a helical shape corresponding to the helically shaped flow surface in each of the sheets of metal;
cutting away a pattern of material from a segment of the cannula proximal to the sheets of metal into the proximal stent region with the plurality of first struts; and
cutting away a pattern of material from a segment of the cannula distal to the sheets of metal into the distal stent region with the plurality of second struts.

15. The method of claim 14 wherein each of the pieces of sheet metal has a length that is greater than a width; and
plastically stretching each of the pieces of sheet metal along the width.

16. The method of claim 14 including a step of expanding the proximal stent region and the distal stent region to stent diameter that is about twice a diameter of the cannula.

17. The method of claim 16 wherein the bending step includes plastically deforming each of the pieces of sheet metal into an open channel extending along the length.

18. The method of claim 17 including elastically compressing the spiral flow inducing stent from the implanted configuration to a transport configuration with a transport diameter that is less than the diameter of the cannula.

19. The method of claim 18 wherein the cutting steps are performed with a laser cutter.

20. The method of claim 19 including electropolishing after the cutting steps.

* * * * *